US006677505B1

(12) United States Patent
Esnault et al.

(10) Patent No.: US 6,677,505 B1
(45) Date of Patent: Jan. 13, 2004

(54) PROMOTER INDUCTIBLE IN PLANTS, SEQUENCE INCORPORATING SAME AND RESULTING PRODUCT

(75) Inventors: Robert Esnault, Gif-sur-Yvette (FR); Dominique Buffard, Chilly-Mazarin (FR); Colette Breda, Voisins-le-Bretonneux (FR); Pierre Coutos-Thevenot, Poitiers (FR); Michel Boulay, Livry-sur-Seine (FR)

(73) Assignee: Champagne Moer and Chandon, Epernay (FR)

( * ) Notice: Subject to any disclaimer, the term of this patent is extended or adjusted under 35 U.S.C. 154(b) by 0 days.

(21) Appl. No.: 09/622,260

(22) PCT Filed: Feb. 12, 1999

(86) PCT No.: PCT/FR99/00315

§ 371 (c)(1),
(2), (4) Date: Nov. 6, 2000

(87) PCT Pub. No.: WO99/41391

PCT Pub. Date: Aug. 19, 1999

(30) Foreign Application Priority Data

Feb. 13, 1998 (FR) .............................. 98 01741

(51) Int. Cl.[7] .......................... A01H 1/00; A01H 11/00; C07H 21/04; C12N 5/00
(52) U.S. Cl. ....................... 800/295; 800/278; 800/279; 435/6; 435/69.1; 435/70.1; 435/320.1; 435/410; 435/418; 435/419; 536/23.1; 536/23.6; 536/24.1; 530/370
(58) Field of Search ................................. 800/295, 278, 800/279; 435/320.1; 536/23.1

(56) References Cited

U.S. PATENT DOCUMENTS

| 5,312,912 A | 5/1994 | Hadwiger et al. .......... 536/24.1 |
| 5,589,610 A | * 12/1996 | De Beuckeleer et al. ... 800/205 |
| 5,677,175 A | * 10/1997 | Hodges et al. ............ 435/320.1 |

FOREIGN PATENT DOCUMENTS

| EP | 0 307 841 | 3/1989 |
| EP | 0 332 104 | 9/1989 |
| WO | WO 93/19188 | 9/1993 |
| WO | WO 94/02619 | 2/1994 |
| WO | WO 94/21793 | 9/1994 |
| WO | WO 95/03690 | 2/1995 |
| WO | WO 95/33818 | 12/1995 |
| WO | WO 97/749277 | 12/1997 |

OTHER PUBLICATIONS

Bevan, "Binary Agrobacterium Vectors For Plant Transformation", Nucleic Acids Research, vol. 12, No. 22, 1984, pp. 8711–8721.
Bejarano et al., "Prospects For Engineering Virus Resistance In Plants With Antisense RNA", Tibtech, vol. 10, 1992, pp. 383–388.
Hain et al., "Disease Resistance Results From Foreign Phytoalexin Expression In A Novel Plant", Nature, vol. 361, 1993, pp. 153–156.
Fischer, "Optimierung Der Heterologen Expression von Stilbensynthasegenen für den Pflanzenschutz", Institute für Biotechnologie des Geschäftsbereichs Pflanzenschutz der Bayer AG, Leverkusen, 1994, pp. 1–158 (Abstract).
Constabel et al., "Stigma– and Vascular–Specific Expression of the PR–10a Gene of Potato: A Novel Pattern of Expression of a Pathogenesis–Related Gene", MPMI, vol. 8, No. 1, 1995 pp. 104–113.
Truesdell et al., "Isolation of Pathogen/Stress–Inducible cDNAs From Alfalfa by mRNA Differential Display".
Breda et al., "Defense Reaction in *Medicago sativa*: A Gene Encoding a Class 10 PR Protein Is Expressed in Vascular Bundles", MPMI, vol. 9, No. 8, 1996, pp. 713–719.
Strittmatter et al., "Inhibition of Fungal Disease Development in Plants by Engineering Controlled Cell Death", Bio/Technology, vol. 13, 1995, pp. 1085–1089.
Vigers et al., "A New Family of Plant Antifungal Proteins", MPMI, vol. 4, No. 4, 1991, pp. 315–323.
Szabados et al., "New Plant Promoter And Enhancer Testing Vectors", Molecular Breeding, vol. 1, 1995, pp. 419–423.
van Loon, "Pathogenesis–Related Proteins", Plant Molecular Biology, vol. 4, 1985, pp. 111–116.
Vera–Estrella et al., "Plant Defense Response to Fungal Pathogens", Plant Physiol, vol. 106, 1994, pp. 97–102.
Scheel et al., "Signals In Plant Defense Gene Activation", Advances in Moleclar Genetics of Plant–Microbe Interactions, vol. 1, pp. 373–380.
Terras et al., "Small Cysteine–Rich Antifungal Proteins from Radish: Their Role in Host Defense", The Plant Cell, vol. 7, 1995, pp. 573–588.
Verma et al., "Small GTP–Binding Proteins and Membrane Biogenesis in Plants[1]", Plant Physiol., vol. 106, 1994, pp. 1–6.
Vigers et al., "Thaumatin–like Pathogenesis–Related Proteins Are Antifungal", Plant Science, vol. 83, 1992, pp. 155–161.
Vaeck et al., "Transgenic Plants Protected From Insect Attack", Nature, vol. 328, 1987, pp. 33–37.
Düring et al, "Antibacterial Resistance Of Transgenic Potato Plants Producing T4 Lysozyme", Advances in Molecular Genetics of Plant–Microbe Interactions, pp. 573–577.

(List continued on next page.)

*Primary Examiner*—Phuong T. Bui
*Assistant Examiner*—Alexander H. Spiegler
(74) *Attorney, Agent, or Firm*—Connolly Bove Lodge & Hutz LLP (57) ABSTRACT

The invention concerns a set of plant promoters inductible by biotic or abiotic stresses, in particular by pathogens, their use, expression vectors comprising said promoters and a gene of interest, cells and/or plants transformed by said vectors. The invention also concerns methods for obtaining said cells and plants, said transformed plants with improved resistance to said pathogens.

23 Claims, 4 Drawing Sheets-

OTHER PUBLICATIONS

Esnault, et al., "Pathological and Molecular Characterizations of Alfalfa Interactions with Compatible and Incompatible Bacteria, *Xanthomonas campestris* pv. alfalfae and *Pseudomonas syringae pv. pisi*", MPMI, vol. 6, No. 5, 1993, pp. 655–664.

Hahn et al., "Pathogen–Defence Gene prp1–1 From Potato Encodes An Auxin–Responsive Glutathione S–Transferase", Eur. J. Biochem., vol. 226, 1994, pp. 619–626.

Kauffman et al., "Biological Function of 'pathogenesis–related' Proteins: Four PR Proteins of Tobacco Have 1,3–β–glucanase Activity", The EMBO Journal, vol. 6, No. 11, 1987, pp. 3209–3212.

Kavanagh et al., "Strategies For Engineering Virus Resistance In Transgenic Plants", Euphytica, vol. 85, 1995, pp. 149–158.

Kinal et al., "Processing and Secretion of a Virally Encoded Antifungal Toxin in Transgenic Tobacco Plants: Evidence for a Kex2p Pathway in Plants", The Plant Cell, vol. 7, 1995, pp. 677–688.

Lagrimini et al., "Molecular Cloning of Complementary DNA Encoding The Lignin–Forming Peroxidase From Tobacco: Molecular Analysis and Tissue–Specific Expression", Proc. Natl. Acad. Sci. USA, vol. 84, 1987, pp. 7542–7546.

Lamb et al., "Emerging Strategies For Enhancing Crop Resistance To Microbial Pathogens",Bio/Technology, vol. 10, 1992, pp. 1436–1445.

Lerner et al., "The Gene For Stinging Nettle Lectin (*Urtica dioica* Agglutinin) Encodes Both A Lectin and a Chitinase", The Journal of Biological Chemistry, vol. 267, No. 16, 1992, pp. 11085–11091.

Liu et al., "Osmotin Overexpression in Potato Delays Development of Disease Symptoms", Proc. Natl. Acad. Sci. USA, vol. 91, 1994, pp. 1888–1892.

Malehorn et al., "Characterization and Expression of an Antifungal Zeamatin–like Protein (Zlp) Gene from *Zea mays*", Plant Physiol., vol. 106, 1994, pp. 1471–1481.

Masoud et al., "Expression of a Cysteine Proteinase Inhibitor (Oryzacystatin–I) in Transgenic Tobacco Plants", Plant Molecular Biology, vol. 21, 1993, pp. 655–663.

Petit et al., "Transformation and Regeneration of the Legume *Lotus corniculatus*: A System For Molecular Studies of Symbiotic Nitrogen Fixation", Mol. Gen. Genet, vol. 207, 1987, pp. 245–250.

Pietrzak et al., "Expression in Plants of Two Bacterial Antibiotic Resistance Genes After Protoplast Transformation With A New Plant Expression Vector", Nucleic Acids Research, vol. 14, No. 14, 1986, pp. 5857–5868.

Toubart et al., "Cloning and Characterization of the Gene Encoding the Endopolygalactronase–Inhibiting Protein (PGIP) of *Phaseolus vulgaris*L." The Plant Journal, vol. 2, No. 3, 1992, pp. 367–373.

Vancanneyt et al., "Construction of an Intron–Containing Marker Gene: Splicing of the Intron in Transgenic Plants and Its Use in Monitoring Early Events in Agrobacterium–Mediated Plant Transformation", Mol. Gen. Genet, vol. 220, 1990, pp. 245–250.

Wu et al., "Disease Resistance Conferred by Expression of a Gene Encoding $H_2O_2$–Generating Glucose Oxidase in Transgenic Potato Plants", The Plant Cell, vol. 7, 1995, pp. 1357–1368.

Cutt et al., "Disease Response to Tobacco Mosaic Virus in Transgenic Tobacco Plants that Constitutively Express the Pathogenesis–Related PR1b Gene", Virology, vol. 173, 1989, pp. 89–97.

Bradley et al., "Elicitor– and Wound–Induced Oxidative Cross–Linking of a Proline–Rich Plant Cell Wall Protein: A Novel, Rapid Defense Response", Cell, vol. 70, 1992, pp. 21–30.

Broekaert et al., "A Chitin–Binding Lectin from Stinging Nettle Rhizomes with Antifungal Properties", Science, vol. 245, 1989, pp. 1100–1103.

Broekaert et al., "Plant Defensins: Novel Antimicrobial Peptides as Components of the Host Defense System", Plant Physiol., vol. 108, 1995, pp. 1353–1358.

Broglie et al., "Transgenic Plants with Enhanced Resistance to the Fungal Pathogen *Rhizoctonia solani*", Science, vol. 254, 1991, pp. 1194–1197.

de Wit, "Molecular Characterization of Gene–For–Gene Systems In Plant–Fungus Interactions And The Application Of A Virulence Genes In Control Of Plant Pathogens", Annu. Rev. Phytopathol, vol. 30, 1992, pp. 391–418.

Ditta et al., "Plasmids Related to the Broad Host Range Vector, pRK290, Useful for Gene Cloning and for Monitoring Gene Expression", Plasmid, vol. 13, 1985, pp. 149–153.

Zhu et al., "Activation of Two Osmotin Like Protein Genes by Abiotic Stimuli and Fungal Pathogen", Plant Physiol. Soil, vol. 108, 1995, pp. 930–937.

Logemann et al., "Expression of a Barley Ribosome—Inactivating Protein Leads to Increase of Fungal Protection In Transgenic Tobacco Plants", Bio/Technology, vol. 10, 1992, pp. 305–308.

Blondon, "Contribution à l'étude du développement des graminés fourragèges : Ray grass et Dactyle" [Contribution to the study of the development of forage grasse : Rye grass and orchard grass], Rev. Gén. Bot., No. 71, 1964, pp. 293–381.

Chet, "Biotechnology in Plant Disease Control", Ecological and Applied Microbiology, pp. 373.

* cited by examiner

FIGURE 1: scheme for isolating the promoter PMs PR 10-1

FIGURE 1a: scheme for isolating the promoter PMs PR10-1 (continued)

FIGURE 2

Figure 3: IND S1 nucleic acid sequence corresponding to the lucerne inducible promoter PMs PR10-1.

Isolated genomic sequence:

```
gaattcttcaaaaaaaaagttgcccttgagaaactaataagttaataaactaagacctctaa
aaaaaaagttaataaactaatatgaatattctctaaacaaaaaataaaactaagaagaatat
attttgcttatttaccagaaaaatactttgcttagtcaaaagaagaagaatattgtgaatta
atttgatactgatgattttttaaagctgtagatatttacgtatttagttaaaaaaatacaatt
attatatatttaattggtgtgtctattcaagtgtttaacttaagttgaggtttattcttatg
ttactaagttggagtggagaagaagactatttgcttgggaggaggaacgcccagtagaatgt
gttattatttttattttttgtaaggagtagagtgtgttatgttgcttgaataattttttt
ttgtaggataatgtattagacaaataaatttggaaacacgaccctgtcaaagagtacacggt
aaaggggggtggtatacaaaagagtgcgtcgctctattcttcaggtcatttggtttgctacag
tttaggaaatttggggaggaaagaaataacagactgtataacgtcaaagaatgctcggttatt
caggtggtagataagattaagtttcttgcttttgcatgggtgaaggcaaagtttgcttctct
tccattcaattaccatgggtggcggcttagtccgtttaccatactggacataggctaagagt
ttttcttttctcgttttttccattacaagttctttatgtaaatactgttttgactttggtgtt
cttcccttagtacaccttgtgctaggaaggactattttgatttggtaatatatttcatttta
acctcttaaaaaaaatcaggaaaagaaaaagataaaggtcggaagtgttacctgattataa
aataaatgattaaattgaaaataaagataaataactaaaatgttttctataattaagttaag
agatgaaatatgtaattttcccaattatatattatgtaagtttttatttatttatatacgt
tgttttgctttgaatttgagtggtcttggaggagagaaaaacaaaagagaaaagaaaaatt
aatagtagatgcaataatttgttagtccaataataatatagttttctttaaaaataatat
catccaaactcatacattaaaaatattattcaaatttatgtcacgtcacaatgagaaaaaat
ggcccaacgaccttgtattacacatcatcgtcatcatcatctaaagtctaaacaatacatct
tcttttcctataaatacaagactcaactccactcataaatcacacaggcaaacaattaactt
cttaatagtttgttatttcacacattag
```

PROMOTER INDUCTIBLE IN PLANTS, SEQUENCE INCORPORATING SAME AND RESULTING PRODUCT

REFERENCE TO RELATED APPLICATION

Application is a 371 of PCT/FR99/00315, filed Feb. 12, 1999 which in turn claims priority to France 98 01741 filed Feb. 13, 1998 Both documents are incorporated by reference for all purposes.

FIELD OF THE INVENTION

The present invention relates to a set of plant promoters which can be induced by biotic or abiotic stresses, in particular by pathogens, to their use, to expression vectors comprising said promoters and a gene of interest, and to cells and/or plants transformed with said vectors. The invention also relates to methods for obtaining said cells or plants, said transformed plants exhibiting improved resistances to said pathogens.

BACKGROUND OF THE INVENTION

Diseases, whether they are of fungal, bacterial or viral origin, are the major problem in viticulture, both in terms of the quality of the musts and of the wines produced (for example *Botrytis cinera,* which is a grey mould agent which attacks the berries at grape-harvesting and leads to bad tastes in the wines), drops in production (for example foliar diseases such as grape downy mildew or grape powdery mildew, attacks by Botrytis on flowers or Fan leaf disease of the grapevine linked to the presence of the virus G.F.L.V., Grape Fan Leaf Virus), or even to that of the survival of the vineyard (for example wood diseases such as eutypiosis or esca syndrome). The conventional control arsenal ranges from simple prophylaxis to plant-protection treatments, biological control to date being used very little.

Chemical control is of course the most widely used method, even though treatments are increasingly being tempered (models for forecasting risks of disease for grape downy mildew for example). With regard to fungicides for example, the French vineyard, which represents approximately 10% of the cultivated land in France, each year uses close to 40% of the fungicides consumed in this country. On a European level, on close to 4 million hectares of vineyard, the 9 to 10 treatments which are carried out each year to control these diseases lead to the use of 120,000 tonnes of fungicidal products.

To cite just the problem of grey mould, it is estimated that over the years 1992 to 1993, 25 to 30% of the 3.7 million hectares of European vineyard were concerned, for a cost of plant-protecting products of 97 and 69 million German Marks (DM), respectively.

The use of these products is not without consequence for the environment (it is the case, for example, for the soil fumigants used to destroy nematodes, which are vectors of the grape fan leaf virus). It also sometimes poses technological problems, with difficulties which can occur during fermentations (the use of sterol biosynthesis inhibitors can block yeast growth at the end of fermentation) and commercial difficulties (procymidone, an anti-Botrytis product, which is sometimes found in wines, hence the American dispute in the years 1990 to 1991).

Moreover, the use of these products has already led to the appearance of resistant strains. This phenomenon has been particularly marked in Champagne and, for some years, the "Comité Interprofessionnel des Vins de Champagne" (CIVC) [Interprofessional Committee of the Wines of Champagne] has recommended not treating against Botrytis.

To overcome these drawbacks, it is imperative to balance the use of plant-protecting products by developing novel methods of control in order to considerably decrease the amounts of products spread over vineyards.

Two approaches are currently envisaged:

Reinforce prophylaxis and decrease the amount of products used (cultivation methods and preventive control, models for forecasting risks of disease, novel spreading materials, novel, more degradable molecules, etc.).

Improve the resistance of the grape varieties to disease.

For this second approach, conventional genetic improvement via the sexual pathway (hybridization with tolerant varieties) is impossible according to French legislation on Appellations d'Origine Contrôlée (A.O.C.) (registered designations of origin) which imposes the grapevine varieties which are to be used for a given appellation (designation). In addition, technically, grapevine, which is a ligneous plant, would require several tens of years to integrate one or more novel resistance properties while at the same time conserving the biochemical and aromatic properties of the grapevine varieties, which are factors of the organoleptic quality of the wines produced.

The control of the regeneration and of the genetic transformation of the grapevine, which has been carried out by the research team of the laboratories of the applicant company since 1988–1990, has made it possible to envisage using the modern techniques of cellular and molecular biology to increase the tolerance of grapevine varieties to fungal diseases.

Henceforth, it is possible, on the one hand, to integrate, into the genome of the grapevine, one or more homologous or heterologous genes which enable the overexpression or expression of a molecule of interest, which is of protein or other nature, and/or the opening of a new biosynthetic pathway and, on the other hand, to regenerate a plant which is more tolerant to one or more diseases, i.e. which has defense mechanisms which are reinforced with respect to the pathogen(s) in question.

There are several different mechanisms of this type in plants. Some can be regarded as being passive and are linked to the physicochemical properties of the cells, epidermal tissues and/or organs of the plant (for example the cuticle or the morphological properties of the grape cluster). Others belong to the dynamics of gene/gene interactions (plant resistance genes and pathogen avirulence genes, mechanisms of host/parasite interactions). These interactions can lead to the development of hypersensitivity reaction (rapid death of the cells of the plant around the point of infection in order to block the colonization of the plant by the fungus, bacterium or virus), but also to the synthesis and to the accumulation of a whole series of compounds. Among these, some can be parietal constituents which are involved in the formation of a "physical" barrier around the point of infection (callose, lignin, hydroxyprolinerich protein, etc.), and others are molecules having antimicrobial functions which are more or less well defined (phytoalexins, pathogen-associated proteins: PR proteins (pathogenesis-related protein), etc.).

The overexpression of these molecules which have antimicrobial functions or which are involved in the formation of a physical barrier around the point of infection can provide plants with a "natural" resistance in response to stresses, in particular stresses of microbial type.

However, constitutive overexpression of this type of protein cannot be envisaged without drawbacks for the plant (energetic cost, slowing down of growth, etc.), which is why it is necessary to envisage the use of inducible promoters and in particular of promoters which are inducible by the stress itself. This is precisely the subject of the present invention.

The present invention relates to a nucleic acid sequence chosen from the group comprising:
  a) the IND S1 sequence,
  b) any sequence corresponding to a fragment of the IND S1 sequence and having a promoter sequence effect in plants.

The invention also relates to promoters in plants, chosen from the group comprising:
  a) the promoter PMs PR10-1 corresponding to the IND S1 sequence,
  b) a promoter of PMs PR10-1 type corresponding to a sequence according to the invention.

Said promoters of PMs PR10-1 type are preferred which exhibit at least 80% homology with the IND S1 sequence. Those which exhibit at least 90% or 95% homology with said sequence are particularly preferred. The promoter sequences in plants which are characterized in that they comprise at least one sequence which is identical to those of the abovementioned promoters are also included in the present invention.

The subject of the invention relates most particularly to the use of the promoters according to the invention for the tissue-specific or non-tissue-specific expression of a gene in a way which is inducible in plants by a biotic or abiotic stress.

Among said biotic stresses according to the invention, the biotic stresses engendered by the attack of a parasite such as a virus, bacterium, yeast or fungus are particularly preferred.

Among said abiotic stresses according to the invention the abiotic stresses engendered by a mechanical wound, such as that caused in particular by an insect or by a physical phenomenon such as wind or frost, are particularly preferred.

The promoters or promoter sequences according to the invention can be used to prepare systems for expression in plants, the systems being able to be inducible and/or constitutive depending on the plant tissues or organs transformed (cf. Examples 2, 3 and 4).

These promoters were obtained from the regulatory sequences of PR protein genes in lucerne. Advantage was taken of the incompatibility response (hypersensitivity reaction, HR) obtained in the host/parasite relationship between lucerne (*Medicago sativa*) and *Pseudomonas syringae* pv *pisi* in order to study the promoter which is responsible for this reaction.

When Pseudomonas attacks lucerne, the appearance of a plant reaction is observed in the region of infection.

The plant material was thus removed following the bacterial attack in order to construct a cDNA library from the messenger RNAs produced in the infected regions adjacent to the necrosis. An amplification by polymerase chain reaction (PCR), using synthetic polynucleotides corresponding to motifs which are conserved in PR protein genes of leguminous plants, made it possible to obtain a radioactive probe which was then used to select transcripts in the cDNA library. Among these, one of them was retained since, after sequencing, it exhibited good homology with equivalent genes encoding PR proteins which are known for other plants (cf. FIGS. 1 and 1a which represent the general scheme of the method for isolating the promoter).

The analysis showed that it corresponded to a gene encoding a class 10 PR protein according to the van Loon (1994) classification. This gene was therefore designated Ms PR10-1 (*Medicago sativa* class 10 PR protein, clone 1).

A subject of the present invention is also systems which are for expressing a gene in plants and which are characterized in that they comprise at least the sequence of said gene under the control of a promoter or of a sequence according to the invention. Among the expression systems according to the invention, expression vectors, and in particular plasmid-type expression vectors, are preferred. Advantageously, said expression vectors are characterized in that they can be transferred into strains of Agrobacterium.

A subject of the invention is also a system or vector for expressing a gene in plants according to the invention, characterized in that it is inducible in plants by a biotic or abiotic stress, preferably a biotic or abiotic stress such as those described above.

The invention also relates to the systems or vectors according to the invention, characterized in that said gene is a gene of interest.

A gene is considered to be a gene of interest if its modification may be desired or used in any type of industry, including agriculture. Besides the already mentioned agriculture, industries such as, for example, the agrofoods industry, the cosmetics industry, the pharmaceutical industry, the chemical industry, etc. will come to mind. This list of examples is not, of course, limiting.

The gene may thus be, for example, a gene of agronomic interest or a gene which enables the plant to produce substances having a value for human or animal nutrition or health. Among the genes of agronomic interest, please note, for example, any gene whose expression makes it possible to modify the physiology of the plant, such as in particular inhibiting, slowing down, accelerating or triggering steps or phenomena which are involved at a given period in the life of the plant, or any gene whose expression makes it possible to improve or decrease the resistance of the plant to physical, chemical or biological attacks. Among the genes of interest which enable the plant to produce substances having a value for human or animal nutrition or health, is meant, for example, the genes which encode pharmaceutical or enzymatic compounds (which can be used for the biosynthesis or biodegradation of organic compounds) or compounds with nutrient value, or genes which make it possible to modify or to inhibit the expression of pharmaceutical, nutrient or toxic compounds or of aromas.

The invention comprises in particular the systems or vectors according to the invention, characterized in that said gene of interest is a gene which is involved in the response to a biotic or abiotic stress, preferably in the response to the inducing biotic or abiotic stress.

Preferably, the invention relates to the systems or vectors according to the invention, characterized in that the biotic stress is the attack of a parasite and the gene of interest is a gene of resistance to said parasite.

Even more preferably, the invention comprises the systems or vectors according to the invention, characterized in that the parasite is a virus, a bacterium, a yeast or a fungus, and the gene of interest is a gene which is involved in the synthesis of a molecule with anti-pathogen action, preferably a gene which is involved in the synthesis of phytoalexins or of PRs.

The constructs which enable the expression of these genes may of course comprise, besides the gene of interest, in particular coding strand 3'-end polyadenylation sequences, as well as enhancer sequences of said gene or of a different gene.

Of course, the constructs will have to be adapted in order to ensure that the gene will be read in correct reading frame with the promoter, and it will obviously be possible to envisage using if this is necessary, several promoters of the same type, as well as several enhancer sequences.

It is also possible to express, with the aid of the promoters according to the present invention, several genes, which are either placed in cascade or carried by different expression systems.

Among the genes of interest which can be expressed by the constructs according to the present invention, mention should be made of the genes which can be placed under the control of the promoter PMs PR10-1 in order to trigger mechanisms of resistance to the plant pathogens which are viroids, viruses, phytoplasmas, bacteria and fungi, or also even the resistance to insects or to ravages (the promoter also being inducible, in tobacco in particular, by wounds).

Among the possible strategies, reference may be made to the reviews by LAMB et al., 1992; VAN LOON et al., 1994; BROOGLIE and BROOGLIE, 1993; CHET, 1993 and to that by PAPPINEN et al., 1994.

By way of example, mention may be made, whether they are homologous or heterologous, of the genes encoding:

hydrolytic enzymes such as chitinases (BROOGLE et al., 1991) or β1-3 glucanases (KAUFFMAN et al., 1987), or combinations of genes encoding these two enzymes, PR proteins (VAN LOON et al., 1994) such as osmotin (LIU et al., 1994, ZHU et al., 1995), thaumatin-like PR-proteins (VIGERS et al., 1992) or class 1 PR proteins (CUTT et al., 1989; HAHN K. and STRITT-MATTER G., 1994), RIP proteins (ribosome Inactivating Protein) of plants (LOGEMANN J. et al., 1992) or of other organisms or microorganisms, proteins which have an inhibitory role for fungus attack enzymes: protease inhibitor (MASOUD et al., 1993), polygalacturonase-inhibiting proteins (TOUBART et al., 1992) or other inhibitory proteins, lectins or chitin binding proteins (BROEKAERT et al., 1989; LERNER and RAIKHEL, 1992), proteins such as (T4) phage or mammalian lysozyme (DURING et al., 1992), proteins which are involved in the phytoalexin biosynthetic pathway (HAIN et al., 1993), antimicrobial peptides such as defensin (BROEKAERT et al., 1995; VIGERS et al., 1991; TERRAS et al., 1995), pathogen-resistance proteins (DE WIT, 1992) which are involved in or trigger hypersensitivity reactions (STRITTMATTER et al., 1995) or enzymes which lead to the production of hydrogen peroxide (WU et al., 1995), proteins which lead to the production of antifungal, antibacterial or anti-insect toxins (KINAL et al., 1995), proteins with peroxidase function which can intervene in lignin polymerization (LAGRIMINI et al., 1987) or in other oxidative reactions (BRADLEY et al., 1992), proteins of viral origin, such as proteins of the shell of viruses in the sense or antisense position (see BEJARANO and LICHTENSTEIN, 1992), proteins which are involved in the synthesis of molecules which trigger the signal transduction chain of stress mechanisms (jasmonic acid, salicylic acid, etc.) or proteins which are themselves involved as a stress signal or intermediates in the transduction chain (systemin, GTP binding proteins) for this, see SCHEEL et al., 1991, VERMA et al., 1994; VERA-ESTRELLA et al., 1994), proteins which are toxic for insects (VAECK et al., 1987). This list is not limiting.

A subject of the present invention is also plant cells which are transformed with a system or vector according to the present invention. Advantageously, said plant cells are grapevine cells and the gene of interest is a gene which confers resistance to a parasite.

The present invention also relates to methods for obtaining cells, characterized in that plant cells are transformed with the aid of a microbiological method which includes an expression system or a vector according to the invention.

Among the most widely used transformation methods, mention should be made in particular of the methods which use Agrobacterluin, whether it is *Agrobacterium tumefaciens* or *Agrobacterium rhizogenes*.

These methods are known, and they will not be described again in detail.

This technology, using plasmid systems, makes it possible to carry out a first transformation of a strain of competent bacteria, generally *E. coli*, which makes it possible to control the structure of the plasmids, and then the strain is used to transfer the recombinant plasmids into strains of agrobacteria which will then be used to transform the plant cells.

The present invention also relates to the transformed plant cells obtained by this method.

The invention also comprises a method for obtaining a plant expressing a gene of interest, characterized in that plant cells of said plant are transformed with the aid of a system or of a vector according to the invention, the cells expressing the gene of interest are selected and a plant is regenerated from said selected cells.

The invention also comprises the plants which comprise a system or a vector according to the invention, and/or cells according to the invention, preferably the plants obtained by implementing a method according to the invention.

It should in particular be noted that the constructs according to the present invention and which use the inducible promoters have made it possible to transform diverse plants, in particular tobacco (*Nicotiana benthamiana*), lucerne (*Lotus corniculatus*) and also grapevine (Vitis sp.).

It has also been possible, moreover, to demonstrate the advantage of the promoter according to the present invention during the regeneration of plants from cells. Specifically, the promoters of equivalent constructs which use strong constitutive promoters have never made it possible to obtain regenerated plants and it might be that the production of defense proteins leads very rapidly to the necrosis of the cells, thus preventing regeneration. This is an additional advantage of the constructs according to the present invention in some systems of plant transformation and regeneration.

Other properties and advantages of the constructs and of the methods according to the present invention may be demonstrated in the examples which follow.

BRIEF DESCRIPTION OF THE DRAWINGS

Restriction sites: E=Eco RI, B=Bam HI.

The values indicated in the figure are expressed in kb (kilobases).

DETAILED DESCRIPTION OF THE INVENTION

EXAMPLE 1

Figure 1:
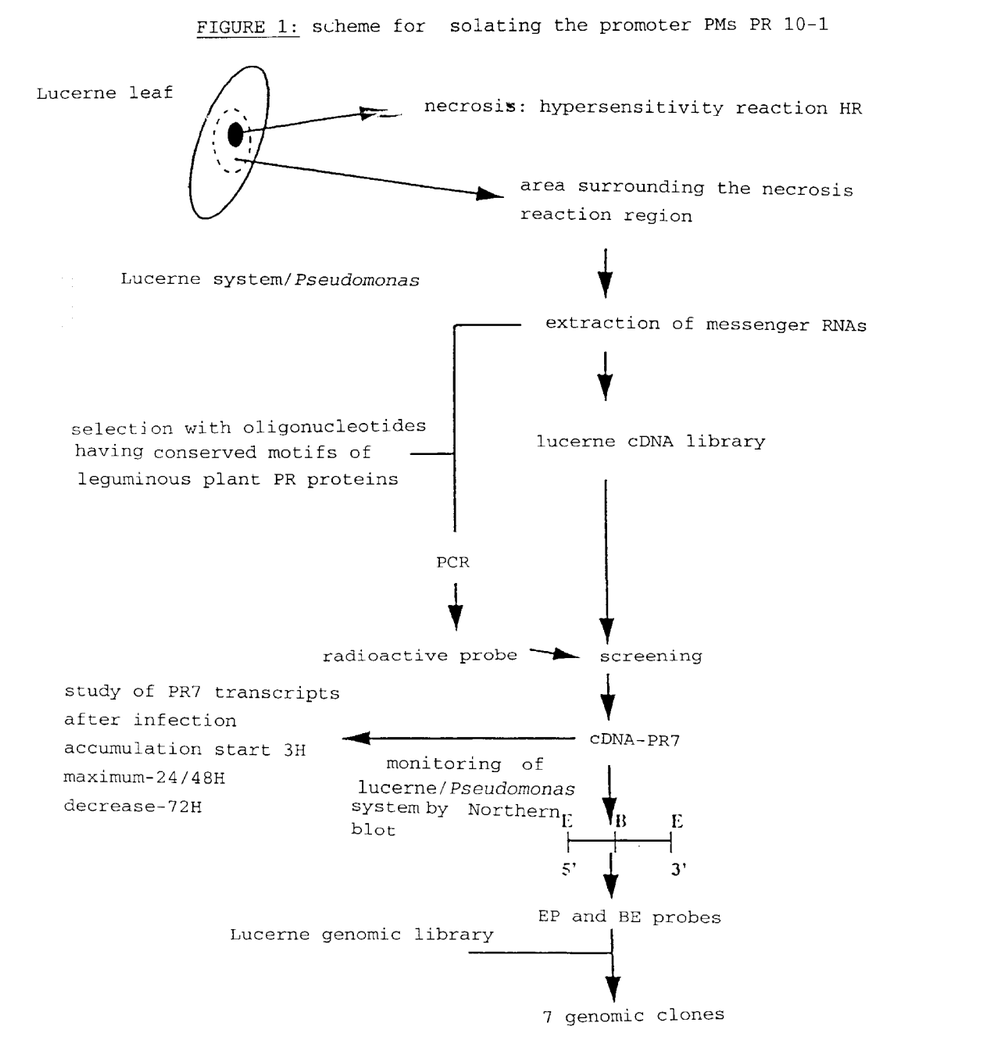
FIGS. 1 and 1a: general scheme representing the various steps of the method for isolating the inducible promoter FMs PR10-1 corresponding to the IND S1 sequence.
Figure 1A:
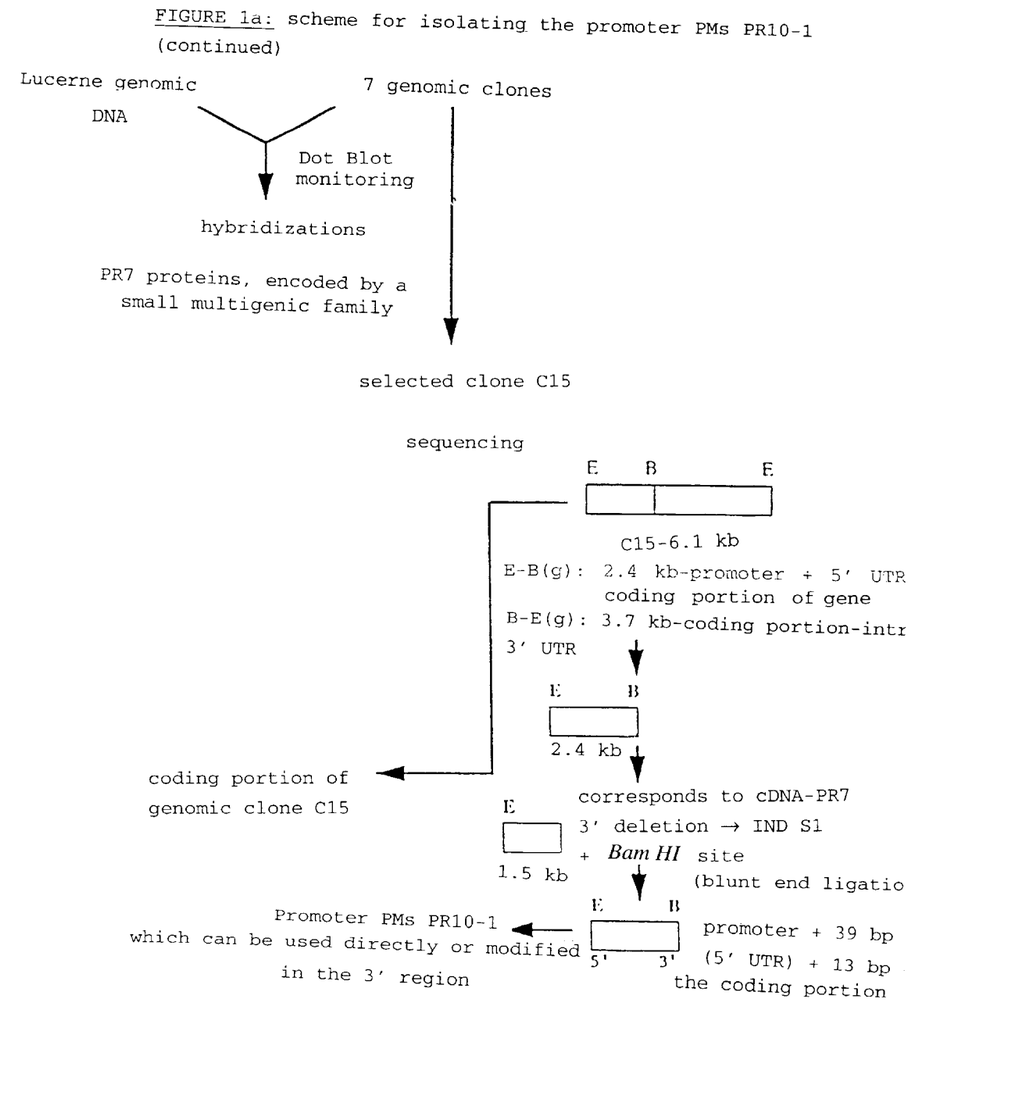

Production of Genomic Clones Comprising Regulatory Sequences of Lucerne PR Protein Genes Production of a Probe for the Purpose of Finding the Promoters (cf. FIGS. 1 and 1a)

The incompatibility response (hypersensitivity reaction: HR) which is obtained in the lucerne (*Medicago sativa*), and *Pseudomonas syringae* pv *pisi* host/parasite relationship made it possible to construct a cDNA library. It was prepared from messenger RNAs which were extracted and purified from the region adjacent to the necrosis caused by the bacterial infection. The samplings of plant material were carried out 6 hours after infiltrating with the bacterial suspension.

In leguminous plants, PR proteins are known to have conserved motifs; this made possible the synthesis of oligonucleotides corresponding to these motifs, which were defined on the basis of sequencing which had already been carried out on pea and soybean PR proteins. A PCR amplification made it possible to obtain a radioactive probe, which was then used to select transcripts from the cDNA library. Among these, one of the clones: cDNA-PR7, was adopted since, after sequencing, it exhibited 87% homology with the genes encoding the pea and soybean PR proteins. The analysis showed that it in fact corresponded to a gene encoding a class 10 PR protein according to the VAN LOON et al. (1994) classification. It was designated Ms PR10-1 (*Medicago sativa* class 10 PR protein, clone 1).

A control, which was carried out in lucerne by Northern blot, showed that the corresponding transcript began to accumulate 3 hours after the infection in the case of the incompatibility response, went through a maximum between 24 and 48 hours and decreased slowly from 72 hours onwards.

This fragment is characterized by the existence of an internal Bam-BI site (marked with a B in FIG. 1) which delimits two portions:

the one, termed 5', of approximately 340 bases, includes the region upstream of the ATG (transcribed but untranslated) and a downstream sequence corresponding to 306 bases, the other, termed 3', corresponds to the end of the coding portion, i.e. 165 bases, and to the untranslated 3' region, i.e. 186 nucleotides from the stop codon to the start of the poly A.

Isolation of Genomic Clones Comprising PR Protein Promoters

Isolation of genomic clones

Figure 2:
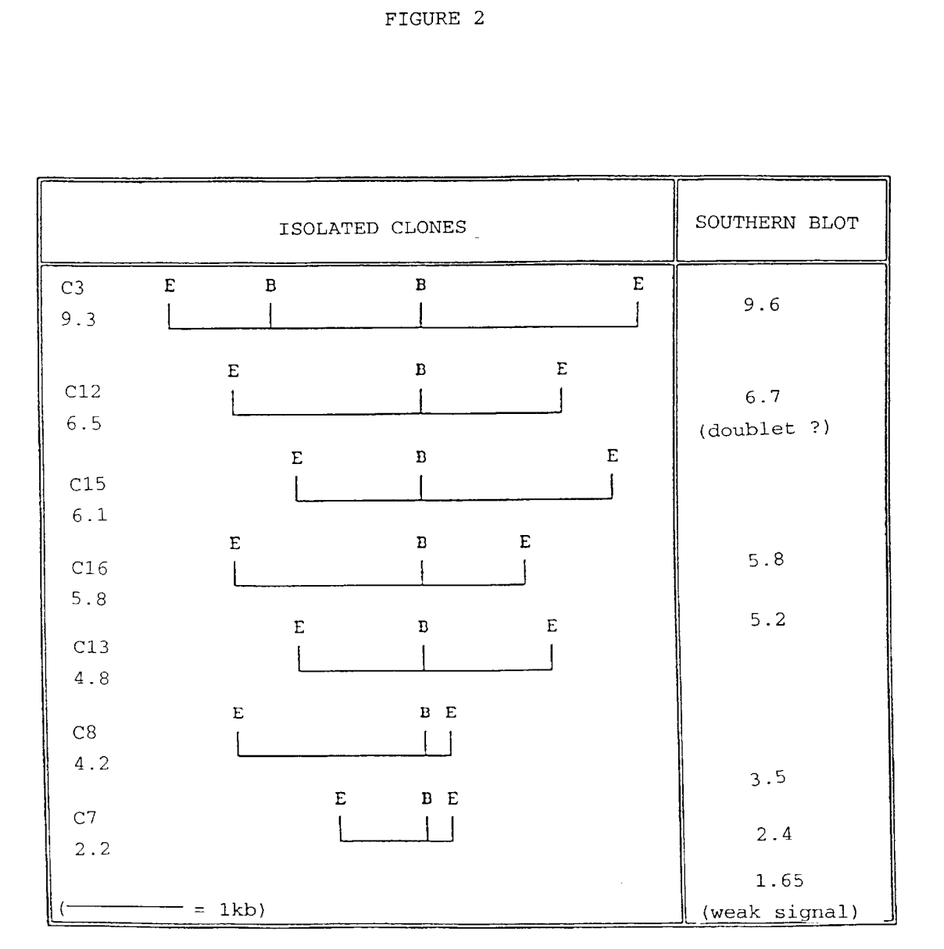
FIG. 2: representation which is of the various clones isolated and corresponds to a Southern blot, hybridized with the 5'- and 3'-portions of DNA-PR7, which are delimited by an internal Bam HI site (B) which was detected in this cDNA.
Figure 3:
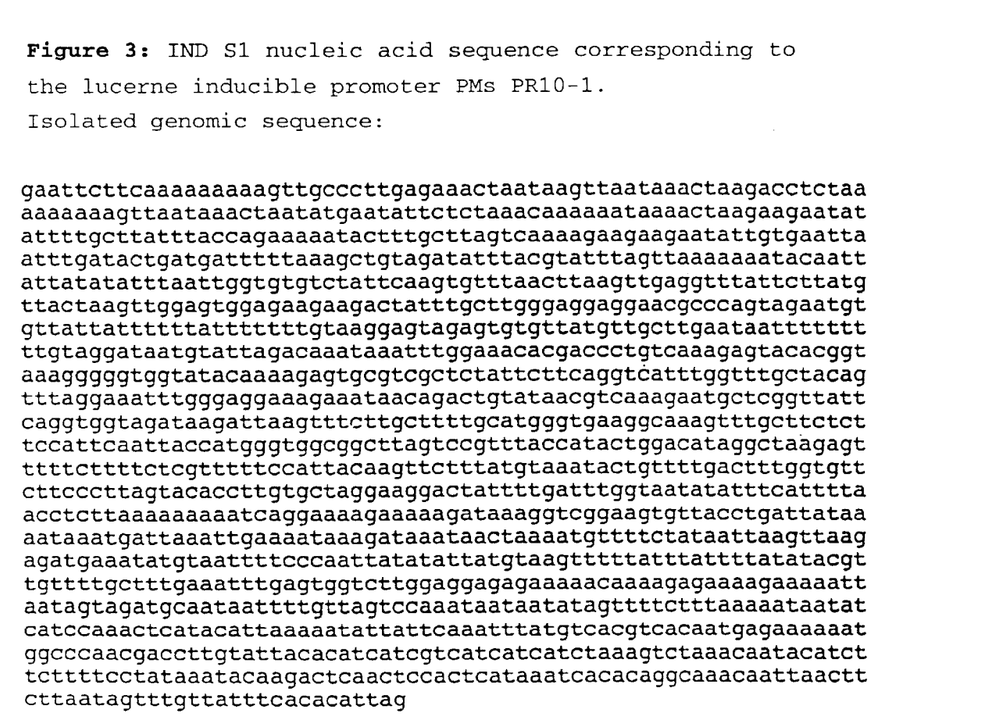
FIG. 3: SEQ ID No.1: DNA sequence corresponding to the IND S1 sequence, which is the isolated genomic sequence of the inducible lucerne promoter PMs PR10-1.

A lucerne genomic library, prepared in EMBL4 (titer: $7 \times 10^8$ p.f.u. (plates forming unit)·ml$^{-1}$), was used on this occasion, and $6 \times 10^5$ p.f.u. were plated out. The 5' fragment of Ms PR10-1 (cDNAPR7) was used as a probe to screen this library and 45 clones gave a signal, which was strong for 13 of them. The restriction mapping and hybridizations, which were carried out with the 5' and 3' fragments of Ms PR10-1, made it possible to conclude that there were 7 distinct clones (cf. FIG. 2). The comparison of the sizes of the 7 clones (9.3; 6.5; 6.1; 5.8; 4.8; 4.2; 2.2 kb) obtained from the screening of the library with that of the bands detected on Southern blot of lucerne genomic DNA showed good agreement between these two types of experimental data (cf. FIG. 2). It was thus possible to deduce therefrom that the genes encoding the PR7 protein corresponded to a small multigenic family.

The fragments (Eco-RI/Eco-RI sites) of these clones (apart from clone C12) were then subcloned in whole or in part, and sequencing was undertaken.

Sequencing carried out

One clone was chosen to be sequenced first, clone C15 (cf. FIG. 1a).

The initial sequencing work demonstrated the presence of an intron of approximately 315 nucleotides in the open reading frame of the gene encoding the PR protein. The clone being studied was then analyzed after digestion with Bam HI (cf. FIG. 1a). Clone C15: 6.1 kb.

The analysis of the clone by Eco RI and Bam HI made it possible to obtain two fragments, E-B (approximately 2.4 kb) and B-E (approximately 3.7 kb). After sequencing and comparing the coding sequence (interrupted by a 600-nucleotide intron) with that of Ms PR10-1 (cDNA-PR7), it appeared that this genomic clone was absolutely identical to this reference cDNA.

Analysis of the expression of the isolated clones in the lucerne-Pseudomonas system The experiments related to clone C15, using the 5' extension technique in order to determine the messenger molecules which were in fact transcribed during the induction of the defense reactions. This technique also has the advantage of making it possible to locate the transcription start site. The results showed that clone C15 was in fact expressed during the induction of the defense reactions in the leaves, during the lucerne/Pseudomonas interaction.

EXAMPLE 2

Genetic Transformations Carried Out in Order to Verify the Promoter Activity of the Isolated Clone Promoter Regions Used Two promoters were adopted for these verification transformations: a control promoter and the PR promoter which was isolated from the lucerne genome and which was derived from C15 (corresponding to the promoter PMs PR10-1).

Ca MV-35S promoter

This promoter, which is a so-called constitutive promoter, is conventionally used. It corresponds to the sequence for regulation of the transcription of the gene of the 35S RNA subunit of the cauliflower mosaic virus (CaMV). The promoter region which was used to prepare the construct with the gus reporter gene in fact corresponds to a fraction of this promoter, which was re-isolated in the form of an Eco RI/Bam HI fragment from the plasmid pDH51 (PIETRZAK et al. , 1986).

PR promoter

The promoter region of genomic clone C15 was studied. This promoter was subsequently termed PMs PR10-1.

PMs PR10-1:

It is derived from the 2.4-kb Eco RI/Bam HI (E/B) fragment of clone C15 FIG. 1a) The integration of this fragment into the binary plasmid, upstream of the reporter gene (see below), was made difficult since there was no restriction site in clone C15 between the TATA box (start of transcription) and the ATG (start of translation). Deletion experiments were therefore carried out until a fragment of approximately 1.5 kb (IND S1 sequence) was obtained. Another Bam HI site was then added, by blunt-end ligation, to the fragment thus obtained in order to enable its insertion upstream of the various coding sequences subsequently used. This fragment thus comprises, with reference to the cDNA which was used to clone it, and besides the upstream promoter region: 39 terminal nucleotides of the 5'UTR (UnTranslated Region) of the Ms PR10-1 gene, located 10 bp from the ATG start codon, the ATG of the Ms PR10-1 gene and a short fragment of its coding region (10 bp), immediately upstream of the integrated Bam HI site. Taking into account the cloning sites, the promoter thus constructed has a potential ATG which might lead to the presence of two ATG codons, a short distance from each other, when constructing chimeric genes. There might then be a risk of modifying the coding frame of the gene used (reporter gene or gene of agronomic interest).

For the transformation experiments with the reporter gene, PMs PR10-1 (PRI) was used in unmodified form after having been cloned into the STRATAGENE Bluescript pSK+/− plasmid. It was possible to re-isolate it in the form of an Eco RI/Bam HI fragment of 1.5 kb approximately.

Plasmids used a) p35S-gus intron (VANCANNEYT et al., 1990)

This plasmid is a derivative of pBin19 (BEVAN, 1984) and, as such, possesses the right and left borders of the binary plasmids, enabling the insertion of the portion contained between these borders into plants using agrobacteria.

The development of the gus-intron (intron derived from the potato LSI gene) reporter gene made it possible to eliminate the false positives (in particular in transient expression) which were due to contaminating agrobacteria. They are unable to splice the introns.

Conventionally, this gene encoding a β-glucoronidase makes it possible to obtain a blue coloration when using a specific substrate (5-bromo-4-chloro-3indolyl-β-glucuronide). This blue colour then indicates that the analysed plant has been transformed and, as a consequence, that the coding sequence of the gene corresponding to the enzyme has been transcribed and, therefore, that the promoter which controls it has been induced.

b) pPR97

This plasmid was constructed by one of the laboratories participating in the project in order to test the effectiveness of promoters (P. RATET, ISV, cited in SZABADOS et al., 1995). It has, in particular, the advantage of possessing a multiple cloning site, which allows transcriptional fusion with the coding frame of the gus gene (*E. coli* uid A) containing the LSI intron. It also possesses some of the properties of the preceding plasmid p35S-gus-intron (borders for integration into the plant genome, selection gene affording resistance to antibiotics such as neomycin: npt II gene).

The activity of the promoter can be revealed and measured by histochemical and enzymatic assays such as GUS.

pPR97 derivatives

Two main constructs were made and subsequently used for transforming model plants.

a) pPR97-35S

The 35S promoter, cloned into the plasmid pDH51 (cf. paragraph below concerning the strains of agrobacteria), was excised and inserted into the multiple cloning site of pPR97, upstream of the reporter gene, in the form of an Eco RI/Bam HI fragment. This plasmid is both a positive control for demonstrating that the construct is functional, and a reference, since the 35S promoter was placed in the same environment as the promoter isolated from the PR protein clones.

b) pPR97-PMs PR10-1

The 1.5 kb were inserted into the same cloning site as that defined above, in this case too in the form of an Eco RI/Bam HI fragment.

c) pG3-3

This made it possible to obtain a strong positive control via a histochemical assay and an enzymatic assay by cloning two 35S promoters in an inverted tandem. The activator sequences of the promoters then act synergistically. The coding frame of the gus-intron gene was then placed under the control of one of the two 35S promoters.

The strains of agrobacteria prepared

The various plasmids were used to transform competent *E. coil* strain DH5α bacteria by heat shock in calcium chloride medium. After selecting the transformed bacteria on medium containing antibiotic (kanamycin) and using a miniprep to verify that they were recombinant, they were used to transfer the recombinant plasmids into strains of agrobacteria by triparental conjugation using the *E. coil* strain HB101 which harbors the autotransferable plasmid pRK2013 (DITITA et al., 1985).

Two strains of agrobacteria were adopted: EHA 105, which is a disarmed *Agrobacterium tumefaciens* and which enables the regeneration of transformed plants (stable transformations), and A4TC24, which is *Agrobacterium rhizogenes* and which was used to obtain the hairy root reaction and composite plants whose roots are transformed but which otherwise have a phenotype which is identical to that of the original phenotype.

Genetic transformations on model plants

Two types of transformation (transient and stable) were carried out using three plant models, *Nicotiana benthamiana, Medicago truncatula* and *Lotus corniculatus*.

The results presented will be mainly those obtained with *N. benthamiana*.

Transient transformations

This first series of experiments was carried out in order to allow rapid verification of the functionality of the constructs prepared with the gus gene in eukaryotic cells.

*N. benthamiana* leaves were thus excised and cocultured on agar medium with the various derivatives of the strain EHA 105. Histochemical assays were then carried out 48 hours after the transformation, and then examined after overnight incubation (12 h).

The control plasmids p35S-gus-intron and pPR97-35S gave a GUS coloration which was positive although weak with the second plasmid.

This weak reactivity without doubt comes from a construction problem, since a portion of the polylinker had to be retained in the vicinity of the transcription start site and of the ATG of the gus gene. Since this polylinker comprises a repeat sequence it can interfere with the transcription of the gene.

The construct pPR97-PMs PR10-1 showed gus gene activity which was similar to that of the 35S gus-intron positive control. This promoter, which was expected to be inducible, thus exhibited an effect which was comparable to a constitutive promoter in this case.

This result can be explained as being the consequence either of the bacterial infection or of the wounds inflicted on the leaves during sampling or during culturing. Since the first hypothesis cannot be verified, the experimental protocol was modified in order to decrease the stress caused to the explants (increase in the osmolarity of the coculture medium using sucrose concentrations of 10 to 30 g.l$^{-1}$, application of a more or less high vacuum range: from 10 to 80 mm of mercury of relative vacuum and creation of more or less severe lesions on the leaves with significant or moderate crushing of the epidermis).

The results showed that as the pressure increased, the number of transformed cells increased. However, a compromise should be found in order to obtain stable transformations, since the many transient transformations obtained in this case frequently turn out to be subsequently lethal for the cells. They are then incapable of giving rise to cali and thus of regenerating shoots and then plants.

Moreover, the inducible nature of the promoter is in part confirmed since, while the coloration due to the 35S gus-intron construct can be detected up to 5 days after coculturing, that obtained with pPR97-PMs PR10-1-gus-intron appears more rapidly at 48 hours but then subsides very rapidly.

Stable transformations a) Tobacco: *N. benthamiana*

A series of transformations was carried out with pPR97-35S, pPR97-PMs PR10-1 and PG3-3. A considerable number of plantlets was obtained with this series of transformations. For each of the plasmids used, an attempt was made to obtain at least 7 acclimatized plants. However, this was not possible for p35S-gus-intron, with which only 5 plants were regenerated and acclimatized. The results obtained are compiled in Table 1.

TABLE 1

Stable transformations obtained in *N. benthamiana* by transformation with the *Agrobacterium tumefaciens* strain EHA 105 and its derivatives.

| Constructs | Cali/explants cultured | Shoots obtained | Plantlets In vivo | Accl |
|---|---|---|---|---|
| p35S-gus-intron | 10 (45) | 6 (1) | 5 | 5 |
| pPr-97-35S gus-intron | 115/122 | 23 | 13 | 12 |
| pPR97-PMs PR10-1 gus-intron | 135/139 | 27 | 20 | 7 |
| pG3-3-35S as an inverted tandem (strong promot.) | not evaluated | 37 | 28 | 20 |

Legend to Table 1

The results are expressed as amount obtained.

Ace.: acclimatized plantlets.

Number of shoots per explant: the number in brackets corresponds to the number of shoots obtained at one month for the first series. For this series (comprising the 35S gus-intron constructs), the cali were left longer on the culture medium in order to obtain a maximum of shoots and thus of plants to acclimatize. For the second series, after one month, a sufficient number of shoots had been obtained and the experiment was then stopped.

Genetic transformations: they are carried out conventionally on 1-cm$^2$ pieces of leaf lamina which are submerged in the Agrobacterium suspension for 30 seconds and then cocultured for 48 hours before being subcultured onto agar medium for cell division and caulogenesis: M. S. (MURASHIGE and SKOOG, 1992), 0.1 mg×l$^{-1}$ NAA (naphthaleneacetic acid), 1 mg×l$^{-1}$ BAP (benzylaminopurine), 400 mg×l$^{-1}$ cefotaxime (elimination of the agrobacteria) and 70 mg×l$^{-1}$ kanamycin (agent for selecting transformed cells). As soon as the first shoots have appeared (approximately one month after coculturing), they are placed on rooting medium which is identical to the former except that it does not contain plant hormones.

The analysis of the results, in terms of the expression of the gus-intron gene, depending on the nature of the promoter which is located upstream of the coding frame of the gene, show that the promoter PMs PR10-1 gives the best results of all of the promoters tested. A more detailed analysis is presented below.

Properties of the promoter PMs PR10-1

Plasmid pPR97-PMs PR10-1-gus-intron

This promoter gave the best results, with differences in constitutive expression of the gus gene depending on the organs tested.

a) Activity in cali

Strong constitutive expression was found. A few minutes of incubation were sufficient to obtain a positive histochemical assay. The promoter is thus strongly induced in this type of material, this being in agreement with the results obtained by VAN LOON (1985). Cali which are cultured in vitro are in a state of stress and, under these conditions, PR proteins are expressed.

b) Activity in acclimatized whole plants Roots

The promoter is induced and the histochemical assay is positive after 2 hours of incubation (as against 5 hours with the 35S promoter). The activity of the gus gene is not uniform in tobacco roots, only the epidermis of the old parts and the apical meristem gave the blue coloration which is characteristic of the assay. According to the literature, defense gene activity in the roots is also observed under conventional conditions.

Flowers

A strong constitutive activity was found in the flowers and, more particularly, in the anthers and the pollen of all the tobacco plants which were transformed with this construct. Gus gene activity was also detected in the trichomas of the sepals and, more weakly, in the petals. These results are also in agreement with those of VAN LOON (1985), which indicate defense gene expression in the floral parts.

Leaves

Weak constitutive gus activity was observed in the trichomas of young leaves of adult plants. In tobacco, the large-leaved rosette stage corresponds to the juvenile stage and the aging stage to that of the formation of seeds. This weak activity was predominantly observed in the multicellular trichomas. To our knowledge, the expression of a PR protein in such structures has never been described.

Constitutive inducing activity of the isolated promoter PMs PR10-1 is thus possible in the trichomas of tobacco leaves (3 plants out of 7), but it appears to be under the influence of the development stages.

In the absence of induction by a pathogen, the activity of the promoter in tobacco is thus limited to the root, to the floral parts (anthers and pollen) and to a few cells of the aerial part (essentially trichomas).

EXAMPLE 3

Other Plant Species Transformed

*Medicago truncatula*

For this species, an attempt was made to produce composite plants, i.e. plants which possess both a wild-type aerial part (not genetically transformed) and transformed roots.

Young germinations were used. After development of the main root, the hypocotyls, which had been excised, were soaked in a suspension of *Agrobacterium tumefaciens* EHA 105 harboring either the plasmid p35S-gus-intron or the plasmid pPR97-PMs PR10-1-gus-intron, so as to subsequently obtain newly formed transformed roots. After one week, roots were obtained and a GUS histochemical assay was carried out. For this experiment, the control consisted of young germinations which were treated in an identical manner to the previous batches (hypocotyls excised, but not soaked in the suspension of agrobacteria).

All the explants of the control batch formed new roots within one week; by contrast, only 50% reacted in the case of the batches treated with the agrobacteria. Whatever the treatment, no root gave a positive response to the GUS assay. Conversely, although necrosed, the base of the hypocotyls in the treated batches often reacted to give a blue coloration (presence of transformed cells). The necrosed part of the explants was then excised, and they were set to rooting again. 50% then developed newly formed roots, some of which proved to be positive in the assay in a few regions.

Chimeric roots (transformed and untransformed cells) were thus obtained, the transformed parts corresponding to cell lines having integrated the construct into a basal stem cell.

The two constructs tested, p35S-gus-intron and pPR97-Pms PR10-a1-gus-intron, gave these transformed root cell lines in 3 and 2 explants, respectively, out of the 6 which were subjected to experiment for each batch.

Although the experimental model is not suited to the study being pursued (study of the expression of PR proteins in the phenomenon of nodulation by Rhizobium), it nevertheless demonstrated that the promoter PMs PR10-1 is just as functional in this plant as in the original plant (*Medicago sativa*).

*Lotus corniculatus*

In this case too, the aim of the experiment was to study the induction of the promoter in nodulation by the symbiotic bacterium *Rhizobium meliloti* NZP 2037 (PETIT et al., 1987). Composite plants were thus produced by transforming hypocotyl cells of young Lotier germinations with *Agrobacterium rhizogenes* strain A4TC24, so as to obtain the hairy root phenomenon (hairy root phenotype). Once this had developed, the main roots were excised and the plantlets were placed in liquid medium to increase the development of the phenomenon. Once the plants were acclimatized, the study of the induction of the promoter(s) was carried out by placing the plantlets under nodulation conditions (BLONDON, 1964). The two promoters which were used for the study were the same as those used in the experiment carried out with *M. trunculata*: 35S and PMs PR10-1. Using these two constructs, less than 10% of the roots having the hairy root phenotype exhibited roots which were positive in the GUS assay. In general, the roots with this phenotype gave fewer nodules than the control roots.

For those obtained with the construct comprising the 35S promoter, only the nodules exhibited a positive response in the GUS assay, whereas for the other (promoter PMs PR10-1), the coloration developed over the whole of the root, apart from the secondary root initiation point. Moreover, this latter construct did not make it possible to obtain nodules on the hairy root-derived roots in interaction with *Rhizobium meliloti*.

EXAMPLE 4

Study of the Hypersensitivity Reaction of Tobacco Transformed with the Constructs which Use the Promoter of the Lucerne PR Gene and the gus-intron Gene Hypersensitivity reaction in *N. benthamiana* transformed with the constructs which combine the promoter of the lucerne PR gene and the gus-intron gene.

Hypersensitivity reaction (HR) assay

The hypersensitivity reaction (HR), developed in the *N. benthamiana/Pseudomonas syringae* pv. *pisi* interaction, was used in this study. Transformed tobacco plants, which had incorporated into their genome the various inserts of the plasmids p35S-gus-intron and pPR97-PMs PR10-1-gus-intron, were acclimatized and then infiltrated with a suspension of *P. syringae* (ESNAULT et al., 1993) at a concentration of $10^9$ bacteria per ml. The solution was injected into the lamina using a hypodermic syringe. Using such a model, the HR-type reaction is regarded as being fully developed after 48 hours. The leaves, which had been infiltrated with the bacterial suspensions, were removed at 24, 48 and 96 hours after inoculation in order to evaluate, by GUS histochemical assay, the induction of the various promoters studied. The analysis of a possible systemic response was also evaluated, using the same histochemical assay, on leaves located below the infiltrated leaf.

Study of the induction of the promoters under HR-type reaction conditions a) 35S constitutive promoter In the case of the 35S constitutive promoter (plasmid pG3-3, for example), the inoculation with *P. syringae* did not modify the response in the assay, and this was evident after a few minutes of incubation. The infiltration with the bacteria does not, therefore, adversely modify the constitutive glucoronidase activity which is obtained with the 35S promoter.

b) Promoter of the PR protein gene: Promoter PMs PR10-1

As shown in Table 2, this promoter is readily inducible by pathogen attack. At 24 hours, the HR-type reaction is not yet fully developed (48 hours for complete display); however, the GUS assay is already positive. In the case of the young transformed tobacco plants which were obtained, the coloration is weak and is located predominantly in the lamina of the infiltrated leaf.

With regard to the systemic response, the response in the leaf which is below the infected leaf, the coloration is only present in the lamina. The adult (with developed stems but not yet having flowered) and juvenile (rosetted) tobacco plants have the same type of response, with weak gus gene activity, as determined by the histochemical assay.

For the older tobacco plants, which are in flower or are bearing seeds, the coloration obtained in the assay is more intense, especially in the veins and the trichomas of the infected leaf, and, in the case of the systemic response, is only in these tissues.

Differences in expression of the reporter gene are thus demonstrated depending on the age of the plant. This response, which is dependent on the development stage, was found in most of the studies carried out on plant PR proteins. The induction of the promoter PMs PR10-1 is a transient phenomenon, since the expression of the reporter gene is no longer visible 96 hours after the inoculation with the bacteria.

The induction is not limited, either, to the HR-type reaction obtained in the plant/bacterium interaction. The same type of response was obtained with the construct PMs PR10-1-gus-intron when one of the plants became infected with a fungus. A homogeneous expression of the gus gene was then visible over the whole of the infected leaf, apart from the region of contamination which, itself, was necrosed.

TABLE 2

Induction of the various promoters studied during the HR-type reaction between *N. benthamiana* and *P. syringae*.

|  | 24 h after inoculation | | 96 h after inoculation |
| --- | --- | --- | --- |
| Construct | Infiltrated leaf | Leaf below | Infiltrated leaf HR-type reaction |
| PMs PR10-1 | 6/7 | 6/7 | 0/3 |
| pG3-3 (35S) | 3/3 | 3/3 | 0/3 |

Legend to Table 2

The results are presented as the number of plants responding positively in the GUS histochemical assay with respect to the number of plants analyzed.

Quantitative Expression of the gus-intron Gene Under the Control of the Various Promoters The method is based on an enzymatic assay.

It uses:

a) a crude extract of the enzyme encoded by the gus gene, which is obtained from transformed tobacco plants, and b) a substrate, p-nitrophenylglucoronide. The rate of hydrolysis of the substrate is monitored using a spectrophotometer and is related to the total amount of proteins in the extract. The method requires, however, the presence of a strong promoter upstream of the gus gene, since it is relatively insensitive.

Consequently, it was not used for assays in which 12 or more hours of incubation with the substrate used for the histochemical assay (X gluc: 5-bromo-4-chloro-3-indolyl-β-glucoronide) were required.

Under these experimental conditions, the 35S promoter, placed in the plasmid pG3-3, gave a rate of substrate hydrolysis (expressed in arbitrary units) which was 5 times higher than with the promoter PMs PR10-1, itself placed in the plasmid pPR97. On the other hand, the promoter PMs PR10-1 gave a stronger expression of the gus gene than did the 35S promoter, when this 35S promoter is placed in the plasmid p35S-gus-intron. Specifically, in this latter case, no substrate hydrolysis was detected.

Similarly, it was not possible to obtain spectrophotometrically detectable values with the other constructs.

Conclusions

The promoter PMs PR10-1, which is isolated from *M. sativa* (lucerne), entirely satisfies the characteristics which are required for its use as a sequence for regulating a gene of agronomic interest which is able to act in plant defense against pathogen attack. It is inducible by a pathogen (bacterium and fungus), this being a process which can take place including in a heterologous system, tobacco. It also has a weak constitutive activity, mainly in the roots, including in other heterologous systems (*M. truncatula* and *L. corniculata*).

Another constitutive activity, which has not yet been explained, has also been noted in the embryonic cali of lucerne.

REFERENCES

BEJARANO E. R. and LICHTENSTEIN C. P., 1992. Prospects for engineering virus resistance in plants with antisense RNA. TIB TECH, 10, 383–387.

BEVAN M., 1994. Binary Agrobacterium vectors for plants transformation Nucl. Acid. Res., 12, 8711–8721.

BLONDON F., 1964. "Contribution à l'étude du développement des graminés fourragères : Ray grass et Dactyle." [Contribution to the study of the development of forage grasses: Rye grass and orchard grass]. Rev. Gén. Bot., 71, 293–381.

BRADLEY D. J., KJELBOM P. AND LAMB C. J., 1992. Elicitor and wound induced oxidative cross-linking of a plant cell wall proline-rich protein: a novel, rapid defense response. Cell, 70, 21–30.

BROEKAERT W. F., VAN PARIJS J., LEYRUS F, JOOS H. and PENMANS W. J., 1989. A chitin-binding lectin from stinging nettle rhizomes with anti-fungal properties. Science, 245, 1100–1102.

BROEKAERT W. F., TERRAS F. R. G., CAMMUE B. P. A. and OSBORN R. W., 1995. Plant defensins: Novel Antimicrobial-peptides as components of the host defense system. Plant Physiol. 108, 1353–1358.

BROOGLE K., CHET I., HOLLIDAY M., CRESSMAN R., BIDDLE P., KNOWLTON C., MAUVAIS C. J. AND BROOGLIE R., 1991. Transgenic plants with enhanced resistance to fungal pathogen *Rhizoctozlia solalti*. Science, 254, 1194–1197.

BROOGLE R., BROOGLE K., 1993. Production of disease-resistant transgenic plants. Curr. Opin. Biotech. 4, 148–151.

CHET I., 1993. Biotechnology in plant disease control, ed. WLEY-LISS XVI, 373 pp illus. WILEY Series in Ecological and Applied Microbiology.

CUTT J. R., HARPSTER M. H., DIXON D. C., CARR J. P., DUNSMUIR P. and KLESSIG D. F., 1989. Distase response to tobacco mosaic virus in tobacco plants that constituvely express the pathogenesis related PR lb gene. VIROLOGY, 173, 89–97.

DE WIT P. J. G. M., 1992. Molecular characterization of gene for gene systems in plant fungus interactions and the application of avirulence genes in control of plant pathogens. Annu. Rev. Phytopathol. 30, 391–418.

DITTA G., SCHNIDTHAUSER T., YACOBSON E., LU P., LIANG A. W. et al., 1985. Plasmid related to the broad range vector, pRK290, useful for gene cloning and for monitoring gene expression. Plasmid, 13, 149–153.

DURING K., FLADUNG M. and LORZ H., 1992. Antibacterial resistance of transgenic potato plants producing T4 lysozyme. Abstract Sixth Intl. Symp. Mol Plant-Microb. Inter, Seattle.

ESNAULT R., BUFFARD D., BREDA C., SALLAUD C., EL TURK J., KONDOROSI A., 1993. Pathological and molecular characterizations of alfalfa interactions with compatible and incompatible bacteria *Xanthomonas campestris* pv. *Alfalfae* and *Pseudomonas syringae* pv. *pisi*. Mol. Plant-Microbe Interact. 6, 655–664.

HAHN K. and STRITTMATTER G., 1994. Pathogen defense gene prp1-1 from potato encodes an auxin-responsive glutathione S Transferase. Eur J. Biochem. 226, 619–626.

HAIN R., REIF H. J., KRAUSE E., LANGEBARTELS R., KINDL H., WORNAM B., WIESE W., SCHMELZER E., SCHREER P. H., STOECKER R. H. and STENZEL K., 1993. Disease resistance results from foreign phytoalexin expression in a novel plant. NATURE, 361, 153–156.

KAUFFMANN S., LEGRAND M., GEOFFROY P., FRITIG B., 1987. Biological function of pathogenesis related proteins: four PR proteins of tobacco have β1–3 glucanase activity. EMBO J.6, 3209–3212.

KAVANAGH T. A. and SPILLANE, 1995. Strategies for engineering virus resistance in transgenic plants. Euphytica, 85, 149–158.

KINAL H., PARK C. M., BERRY J. O., KOLTIN Y. and BRUENN J. A., 1995. Processing and secretion of virally encoded antifungal toxin in transgenic tobacco plants: Evidence for a Kex 2p. pathway in plants. Plant Cell 7, 677–688.

LAGRIMINI L. M., BURKHART W., MOYER M. and ROTHSTEIN S., 1987. Molecular cloning of complementary DNA encoding the lignin forming peroxidase from tobacco: Molecular analysis and tissue specific expression. Proc. Nat. Acad. Sci. USA 84, 7542–7546.

LAMB C. J., RYALS J. A., WARD E. R., DIXON R. A., 1992. Emerging strategies for enhancing crop resistance to microbial pathogens. Bioltechnology 10, 1436–1445.

LERNER D. R. and RAIKHEL N. V., 1992. The gene for stinging nettle lectin (*Urtica dioica* agglutin) encodes both a lectin and a chitinase. J. Biol. Chem. 267, 11085–11091.

LIU D., RAGHOTHAMA K. G., HASEGAWA P. M., BRESSAN R. A., 1994. Osmotin over expression in potato delays development of disease symptoms. Proc. Nat. Acad. Sci. USA 91, 1888–1892.

LOGEMANN J., JACH G., TOMMERUP H., MUNDY J. and SCHELL J., 1992. Expression of a Barley Ribosome-Inactivating Protein leads to increase of fungal protection in transgenic tobacco plants. Bio/technology, 10, 305–308.

MALEHORN D. E., BORCMEYER J. R., SMITH C. E. and SHAH D., 1994. Characterization and expression of an antifungal zearnatin-like protein (Z1p) gene from zen mays. Plant Physiol. 106, 1471–1481.

MASOUD S. A., JOHNSON L. B., WHITE F. F. and REECK G. R., 1993. Expression of a cysteine proteinase inhibitor in transgenic tobacco plants. Plant Mol. Biol. 21, 655–663.

MURASHIGE T. and SKOOG F., 1962. A revised medium for rapid growth and bioassay with tobacco tissue cultures. Physiol. Plant. 15, 473–497.

PAPPINEN A., KEINOWEN MATAELAE K., SUSI A., Von WEISSENBERG K., 1994. Molecular biology of resistance to insects and diseases in birch and pines. Abstract Proc. Application of Biotechnology to tree culture, protection and utilization. USDA For. Serv. Gen. Tech. Rep. NC 175 page 31.

PETIT A., STOUGAARD J., KUHLE A., MARCKER K. A. and TEMPE J., 1987. Transformation and regeneration of the legume: *Lotus corniculatus*. A system for molecular studies of symbiotic nitrogen fixation. Mol. Gen. Genet. 207, 245–250.

PIETRZAK M., SHILLITO R. D., HOHN T. and POTRYKUS I., 1986. Expression in plants of two bacterial antibiotic genes after protoplast transformation with a new plant expression vector. Nucl. Acids Res. 14, 5857–5869.

SCHELL D., COLLING C., HEDRICH R., KAWALLECK P., PARKER J. E., SACKS W. R., SOMSSICH I. E. and HAHLBROCK K., 1991. Signal in plant defense gene activation. Adv. Mol. Genet. Plant Microb. Inter. VI, HENNECKE H. and VERMA DPS (eds), KLUMER, Dordrecht, The Netherlands p 373–380.

STRITTMATTER G., JANSSENS J., OPSOMER C. and BOTTERMAN J., 1995. Inhibition of fungal disease development in plants by engineering controlled cell death BIO/TECHNOLOGY 13, 1085–1098.

SZABADOS L., CHARRIER B., KONDOROSI A., De BUIJN F. T. and RATET P., 1995. New promoter and enhancer testing vectors. Mol. Breeding.

TERRAS F. R., EGGERMONT K., KOVALEVA V., RAIKHEL N. V., OSBORN R. W., KESTER A., REES S. B., TORREKENS S., VAN LEUVEN F., VAN DER LEYDEN J., CAMUE B. P. A. and BROEKAERT W. F., 1995. Small cystein-Rich Antifungal Proteins from Radish: Their Role in Host Defense. Plant Cell 7, 573–588.

TOUBART P., DESIDERIO A., SALVI G., CERVONE F., DARODA L., DE LORENZO G., BERGMAN C., DARVILL A. G. and ALBERSHEIM P., 1992. Cloning an characterization of the gene encoding the endo Poly Galacturonase-Inhibiting Protein (PGIP) of *Phaseolus vulgaris*. Plant J. 2, 367–373.

VAECK M., REYNAERTS A., HOFTE H., JANSENS S., DE BEUCKELEER M., DEAN C., ZABEAU H., VAN MONTAGU M., LEEMANS J., 1987. Transgenic plants protected from insect attack. Nature 327, 33–37.

VANCANNEYT G., SCHMIDT R., O'CONNOR-SANCHEZ A., WILLMETZER L. and ROCHA-SOZA M., 1990. Construction of an intron-containing marker-gene: splicing of the intron in transfenic plants and its use in monitoring early events in Agrobacterium-mediated transformation. Mol. Gen. Genet. 220, 245–250.

VAN LOON L. C., 1985. Pathogenesis Related Proteins. Plant Mol. Biol. 4, 111–116.

VAN LOON L. C., PIERPOINT W. S., BOLLER T., CONEJERO V., 1994. Recommendations for naming plant pathogenesis related proteins. Plant Mol. Biol. Rep. 12, 245–264.

VERA-ESTRELLA R., HIGGINS V. J. and BLUMWALD E., 1994. Plant Defense Response to Fungal Pathogens II. G Protein-Mediated Changes in Host Plasma Membrane Redox Reactions. Plant Physiol. 106, 97–102.

VERMA D. P. S., CHEON CHONG III and HONG Z., 1994. Small GTP Binding Proteins and Membrane Bi9genesis in Plants. Plant Physiol. 106, 1–6.

VIGERS A. J., ROBERTS W. K., SELITRENNIKOFF C. P., 1991. A New Family of Plant Antifungal Proteins. Mol. Plant-Microbe Interact. 4, 315–323.

VIGERS A. J., WIEDEMANN S., ROBERTS W. K., LEGRAND M., SELITRENNIKOFF C. P. and FRITIG B., 1992. Thaumatin-like pathogenesis-related proteins are antifungal. Plant Science, 83, 155–161.

WU G., SHORTT B. J., LAWRENCE E. B., LEVINE E. B., FITZSIMMONS K. C. and SHAM D. M., 1995. Disease resistance conferred by expression of a gene encoding H2O2 generating glucose oxidase in transgenic potato plants. Plant Cell, 7, 1357–1368.

ZHU B., CHEN T. H. H. and LI P. H., 1995. Activation of two osmotin like protein genes by abiotic stimuli and fungal pathogen. Plant Physiol. Soil. 108, 930–937.

What is claimed is:

1. A promoter comprising an isolated nucleic acid sequence consisting of SEQ ID NO. 1.

2. A method for tissue-specific or non-tissue specific expression of a heterologous sequence obtained from a plant and under the control of a promoter consisting of SEQ ID NO: 1, wherein the expression of said heterologous sequence is inducible by biotic or abiotic stress, said method comprising the steps of:

providing a polynucleotide sequence comprising an isolated promoter sequence consisting of SEQ ID NO: 1;

operably linking said heterologous sequence to said polynucleotide sequence;

transforming a plant with said polynucleotide sequence operably linked to said heterologous sequence; and expressing said heterologous sequence under biotic or abiotic stress conditions.

3. The method, according to claim 2, wherein said biotic stress is caused by a parasite.

4. The method, according to claim 3, wherein said parasite is a virus, a bacterium, a yeast or a fungus.

5. The method, according to claim 2, wherein said abiotic stress is a mechanical wound.

6. The method, according to claim 5, wherein said mechanical wound is caused by an insect.

7. An expression vector for expressing a heterologous DNA sequence comprising:

at least one heterologous DNA sequence; and a promoter comprising an isolated nucleic acid sequence selected from the group consisting of SEQ ID NO. 1 and a portion of SEQ ID NO. 1, wherein said portion of SEQ. ID. NO.: 1 retains promoter activity and, wherein said at least one heterologous DNA sequence is under the control of said promoter.

8. An expression vector according to claim 7, wherein said vector is a plasmid.

9. An expression vector according to claim 7, wherein said vector can be transformed into *Agrobacterium*.

10. An expression vector according to claim 7, wherein said vector is inducible in plants by a biotic or abiotic stress.

11. The expression vector according to claim 7 wherein said heterologous DNA sequence is expressed in the response to a biotic or abiotic stress.

12. The expression vector according to claim 11 wherein said heterologous DNA sequence is expressed in the response to the inducing biotic or abiotic stress.

13. The expression vector according to claim 12 wherein said biotic stress is caused by a parasite and said heterologous DNA sequence codes for resistance to said parasite.

14. The expression vector according to claim 13 wherein said parasite is a pathogen selected from the group consisting of a virus, a bacterium, a yeast, and a fungus, and said heterologous DNA sequence is involved in the synthesis of a molecule with anti-pathogenic activity.

15. An expression vector according to claim 14 wherein said molecule with anti-pathogenic activity is selected from the group consisting of phytoalexins and PR proteins.

16. A plant cell transformed by a vector according to claim 7.

17. A plant cell according to claim 16, wherein said cell is a grapevine cell.

18. The plant cell, according to claim 16, wherein said heterologous DNA sequence encodes a protein which renders a plant resistant to a parasite, wherein said plant cell expresses said heterologous DNA sequence.

19. A plant comprising cells according to claim 16.

20. A method for obtaining a transformed plant cell, comprising transforming a plant cell using vector according to claim 7.

21. A method for obtaining a plant expressing a heterologous DNA sequence comprising the steps of transforming cells of said plant using a vector according to claim 7;

expressing said heterologous DNA sequence in the transformed cells;

selecting for cells expressing said heterologous DNA sequence; and regenerating a plant from said the selected cells expressing said heterologous DNA sequence.

22. A plant obtained by the method according to claim 21.

23. A plant comprising a vector according to claim 7.

* * * * *

SEQUENCE LISTING

<160> NUMBER OF SEQ ID NOS: 1

<210> SEQ ID NO 1
<211> LENGTH: 1392
<212> TYPE: DNA
<213> ORGANISM: Medicago sativa

<400> SEQUENCE: 1

```
gaattcttca aaaaaaagt tgcccttgag aaactaataa gttaataaac taagacctct        60 aaaaaaaag ttaataaact aatatgaata ttctctaaac aaaaaataaa actaagaaga       120
atatattttg cttatttacc agaaaaatac tttgcttagt caaaagaaga agaatattgt      180
```

-continued

```
gaattaattt gatactgatg atttttaaag ctgtagatat ttacgtattt agttaaaaaa    240
atacaattat tatatattta attggtgtgt ctattcaagt gtttaactta agttgaggtt    300
tattcttatg ttactaagtt ggagtggaga agaagactat ttgcttggga ggaggaacgc    360
ccagtagaat gtgttattat tttttatttt tttgtaagga gtagagtgtg ttatgttgct    420
tgaataattt tttttgtag gataatgtat tagacaaata aatttggaaa cacgaccctg     480
tcaaagagta cacggtaaag ggggtggtat acaaagagt gcgtcgctct attcttcagg     540
tcatttggtt tgctacagtt taggaaattt gggaggaaag aaataacaga ctgtataacg    600
tcaaagaatg ctcggttatt caggtggtag ataagattaa gtttcttgct tttgcatggg    660
tgaaggcaaa gtttgcttct cttccattca attaccatgg gtggcggctt agtccgttta    720
ccatactgga cataggctaa gagtttttct tttctcgttt ttccattaca agttctttat    780
gtaaatactg ttttgacttt ggtgttcttc ccttagtaca ccttgtgcta ggaaggacta    840
ttttgatttg gtaatatatt tcattttaac ctcttaaaaa aaaatcagga aaagaaaaag    900
ataaaggtcg gaagtgttac ctgattataa aataaatgat taaattgaaa ataaagataa    960
ataactaaaa tgttttctat aattaagtta agagatgaaa tatgtaattt tcccaattat   1020
atattatgta agtttttatt tattttatat acgttgtttt gctttgaaat ttgagtggtc   1080
ttggaggaga gaaaaacaaa agagaaaaga aaaattaata gtagatgcaa taattttgtt   1140
agtccaaata ataatatagt tttctttaaa aataatatca tccaaactca tacattaaaa   1200
atattattca aatttatgtc acgtcacaat gagaaaaaat ggcccaacga ccttgtatta   1260
cacatcatcg tcatcatcat ctaaagtcta aacaatacat cttcttttcc tataaataca   1320
agactcaact ccactcataa atcacacagg caaacaatta acttcttaat agtttgttat   1380
ttcacacatt ag                                                       1392
```